United States Patent
Kweon et al.

(10) Patent No.: US 11,254,641 B2
(45) Date of Patent: Feb. 22, 2022

(54) INTERMEDIATES FOR OPTICALLY ACTIVE PIPERIDINE DERIVATIVES AND PREPARATION METHODS THEREOF

(71) Applicant: HK inno.N Corporation, Seoul (KR)

(72) Inventors: Jae Hong Kweon, Gyeonggi-do (KR); Eun Sun Kim, Gyeonggi-do (KR); Hyuk Woo Lee, Gyeonggi-do (KR); Dong Hyun Ko, Gyeonggi-do (KR); Chae Young Ryu, Gyeonggi-do (KR); Kwang Do Choi, Gyeonggi-do (KR); SeungPyeong Heo, Seoul (KR)

(73) Assignee: HK inno.N Corporation, Seoul (KR)

( * ) Notice: Subject to any disclaimer, the term of this patent is extended or adjusted under 35 U.S.C. 154(b) by 0 days.

(21) Appl. No.: 16/771,463

(22) PCT Filed: Dec. 7, 2018

(86) PCT No.: PCT/KR2018/015559
§ 371 (c)(1),
(2) Date: Jun. 10, 2020

(87) PCT Pub. No.: WO2019/117550
PCT Pub. Date: Jun. 20, 2019

(65) Prior Publication Data
US 2021/0107873 A1 Apr. 15, 2021

(30) Foreign Application Priority Data

Dec. 11, 2017 (KR) ........................ 10-2017-0169227

(51) Int. Cl.
*C07C 69/76* (2006.01)
*C07D 211/74* (2006.01)
*B01J 21/18* (2006.01)
*B01J 23/44* (2006.01)

(52) U.S. Cl.
CPC ............. *C07D 211/74* (2013.01); *B01J 21/18* (2013.01); *B01J 23/44* (2013.01); *C07C 69/76* (2013.01); *C07B 2200/07* (2013.01)

(58) Field of Classification Search
None
See application file for complete search history.

(56) References Cited

U.S. PATENT DOCUMENTS 5,846,980 A * 12/1998 El Ahmad ............ C07D 209/08
514/317
2012/0041225 A1 2/2012 Vaidya

FOREIGN PATENT DOCUMENTS

| IN | 20112383 | 7/2011 |
|---|---|---|
| JP | 2003506369 | 2/2003 |
| JP | 2013528656 | 7/2013 |
| JP | 2014521715 | 8/2014 |
| KR | 1020110036191 A | 4/2011 |
| SU | 606310 | 5/1984 |
| WO | WO2004094380 | 11/2004 |
| WO | WO2009015164 A2 | 1/2009 |
| WO | WO2011159852 A1 | 12/2011 |
| WO | WO2013021052 A1 | 2/2013 |
| WO | WO2013116491 A1 | 8/2013 |

OTHER PUBLICATIONS

RU Office Action in Russian Appln. No. 2020122729/04(039128), dated Feb. 5, 2021, 16 pages with English Translation.
Office Action for KR10-2017-0169227 dated May 18, 2019. 10 pages.
Office Action for KR10-2019-0124891 dated May 30, 2020. 9 pages.
International Search Report for PCT/KR2018/015559 dated Mar. 27, 2019. 4 pages.
Written Opinion of the International Searching Authority dated Mar. 27, 2019. 5 pages.
European Extended Search Report in EP Appln. No. 18889663.3, dated Jul. 14, 2021, 6 pages.
Japanese Office Action in JP Appln. No. 2020-550575, dated Jun. 1, 2021, 9 pages with English Translation.

* cited by examiner

*Primary Examiner* — Sudhakar Katakam
*Assistant Examiner* — Jennifer C Sawyer
(74) *Attorney, Agent, or Firm* — Fish & Richardson P.C.

(57) ABSTRACT

A preparation method according to the present invention makes it possible to industrially produce large amounts of highly pure optically active tert-butyl 3-methyl-4-oxopiperidine-1-carboxylate in high yield by use of commercially available reagents and solvents. In addition, the use of novel intermediates according to the present invention makes it possible to produce highly pure optically active tert-butyl 3-methyl-4-oxopiperidine-1-carboxylate in high yield.

3 Claims, No Drawings

INTERMEDIATES FOR OPTICALLY ACTIVE PIPERIDINE DERIVATIVES AND PREPARATION METHODS THEREOF

TECHNICAL FIELD

The present invention relates to intermediates for optically active piperidine derivatives and preparation methods thereof.

BACKGROUND ART

Piperidine derivatives are widely used as key pharmacophores in the pharmaceutical and chemical fields. In particular, International Patent Publication Nos. WO 2004/041777, WO 2009/106534, WO 2008/119718, WO 2010/051374, WO 2005/040169, WO 2013/021052, WO 2004/058709, WO 2016/120849, WO 2014/023815, WO 2013/181579, WO 2016/120850 and the like disclose tert-butyl 3-methyl-4-oxopiperidine-1-carboxylate as an intermediate for synthesizing various drugs, and also disclose the methods shown in Reaction Schemes I to III as methods for preparing the intermediate:

[Reaction Scheme I]

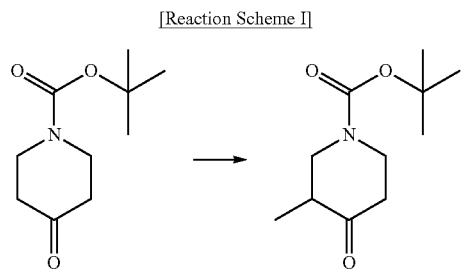

[Reaction Scheme II]

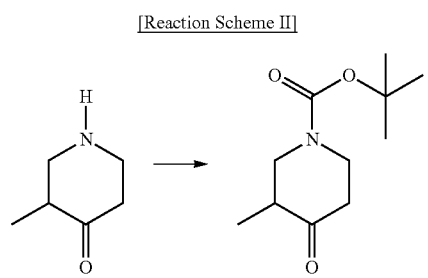

[Reaction Scheme III]

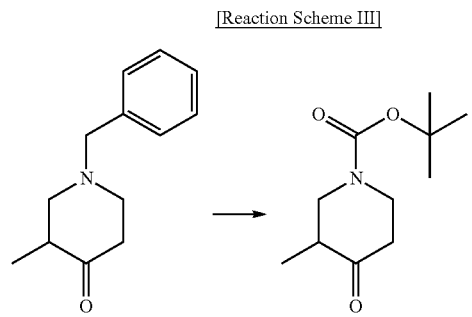

However, the intermediate compound disclosed in the above-mentioned patent documents is a racemate, and the methods for preparing the same can also prepare only a racemate. In addition, these patent documents do not disclose any method for preparing optically active tert-butyl 3-methyl-4-oxopiperidine-1-carboxylate.

However, pharmaceutical drugs may have significantly different pharmacological activities and side effects, and for this reason, many pharmaceutical drugs have been developed as specific isomers. Preparation of pharmaceutical drugs using specific isomeric tert-butyl 3-methyl-4-oxopiperidine-1-carboxylate as an intermediate have problems arise in that it is economically inefficient due to a large amount of consumption of reagents and is not suitable for mass production due to its low production yield, compared to when pharmaceutical drugs are prepared using racemic tert-butyl 3-methyl-4-oxopiperidine-1-carboxylate as an intermediate.

Accordingly, the present inventors have developed a method capable of industrially producing large amounts of highly pure optically active tert-butyl 3-methyl-4-oxopiperidine-1-carboxylate, which is useful as an intermediate in the pharmaceutical and chemical fields, in high yield by use of commercially available reagents and solvents, thereby completing the present invention.

DISCLOSURE OF INVENTION

Technical Problem

The present invention is intended to provide a method capable of industrially producing large amounts of highly pure optically active tert-butyl 3-methyl-4-oxopiperidine-1-carboxylate, which is useful as an intermediate in the pharmaceutical and chemical fields, in high yield by use of commercially available reagents and solvents.

The present invention is also intended to provide novel intermediates useful for the preparation of tert-butyl 3-methyl-4-oxopiperidine-1-carboxylate.

Solution to Problem

To achieve the above objects, the present invention provides a method for preparing a compound of the following formula IV, comprising a step (step 1) of preparing a compound of the following formula II by optically resolving a compound of the following formula I:

[Formula I]

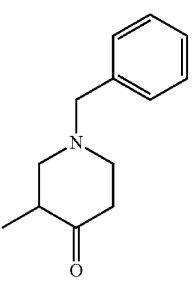

[Formula II]

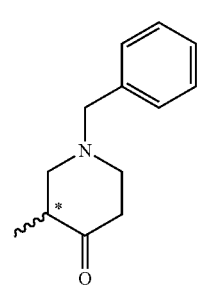

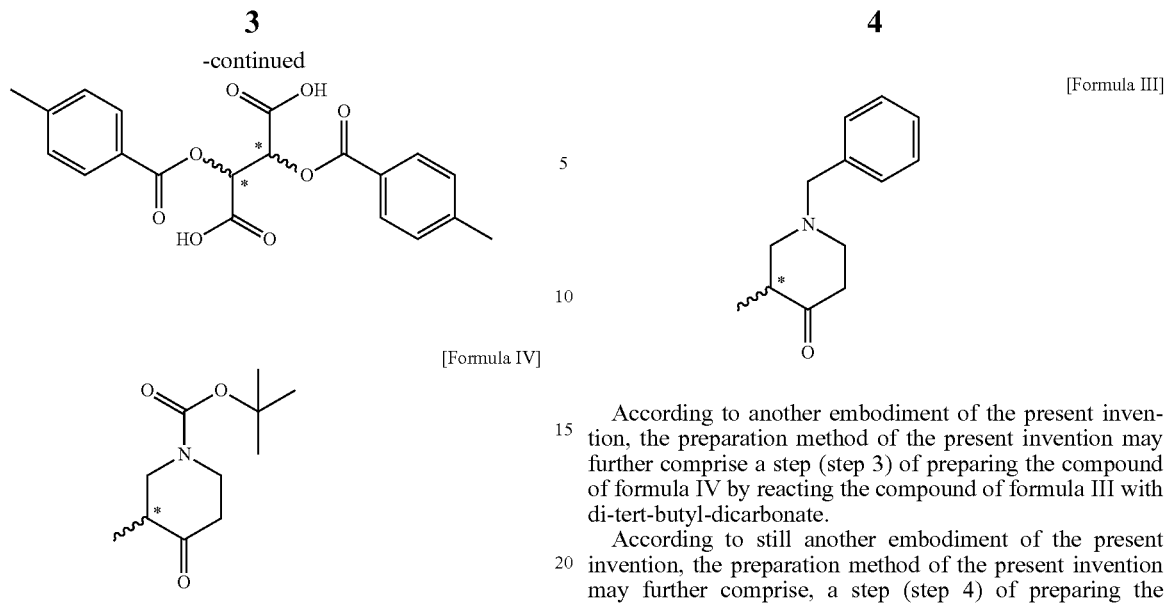

According to an embodiment of the present invention, the preparation method of the present invention may further comprise a step (step 2) of preparing a compound of the following formula III by reacting the compound of formula II with a base:

According to another embodiment of the present invention, the preparation method of the present invention may further comprise a step (step 3) of preparing the compound of formula IV by reacting the compound of formula III with di-tert-butyl-dicarbonate.

According to still another embodiment of the present invention, the preparation method of the present invention may further comprise, a step (step 4) of preparing the compound of formula I by racemizing an opposite enantiomer, which remains after preparing the desired optically active compound of formula II in step 1, in the presence of a base, and recycling the produced compound to step 1.

In the present invention, step 1 to step 4 as described above may generally be rep-resented by Reaction Scheme 4 below:

[Reaction Scheme IV]

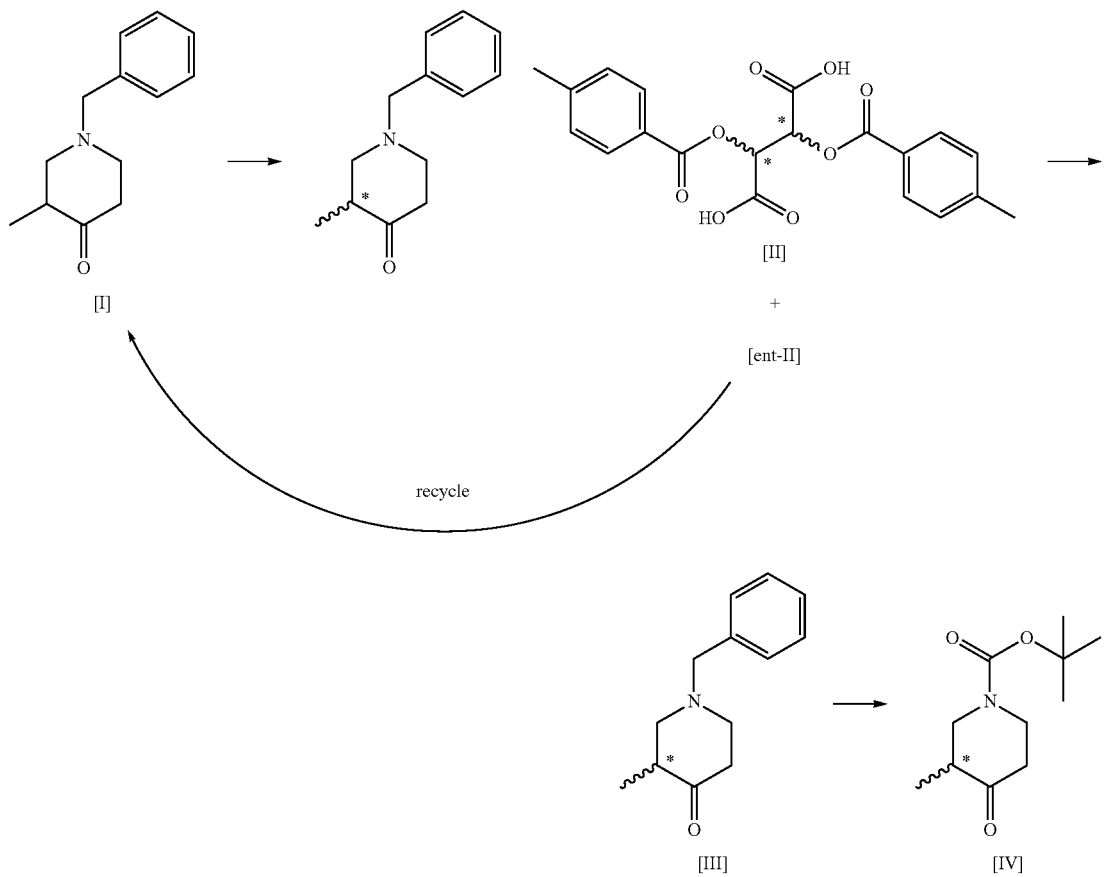

Hereinafter, each step will be described in detail.

In the present invention, step 1 is a step of coupling the compound of formula I with a compound of the following formula V-1 or V-2:

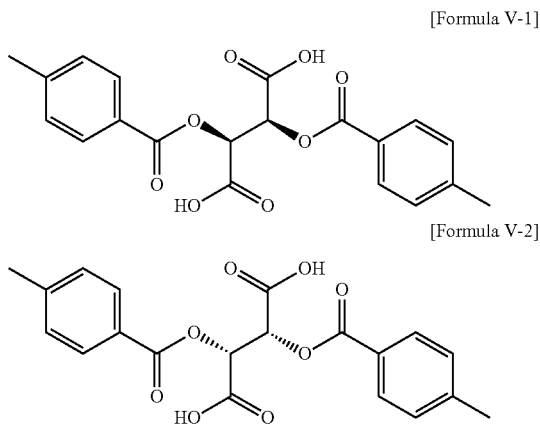

[Formula V-1]

[Formula V-2]

The compound of formula V-1 or V-2 may be an anhydride or a hydrate.

In addition, a solvent that is used in step 1 is not limited and may be any solvent in which the reaction of step 1 may be performed. For example, the reaction of step 1 may be performed in methanol, ethanol, isopropanol, acetone, acetonitrile, ethyl acetate, dichloromethane, tetrahydrofuran, or a mixture solvent thereof.

Furthermore, the reaction of step 1 may be performed at a temperature of 0 to 50° C., preferably 35 to 45° C.

In the present invention, the base that is used in step 2 above is not limited and may be any base in which the reaction of step 2 may be solvent. For example, ammonium hydroxide, sodium hydroxide, potassium hydroxide or lithium hydroxide may be used as the base. Furthermore, the pH is preferably adjusted to 9.8-10.5 by use of the base.

Moreover, a solvent that is used in step 2 is not limited and may be any solvent in which the reaction of step 2 may be performed. For example, the reaction of step 2 may be performed in dichloromethane, ethyl acetate, methyl ethyl ketone, or a mixture solvent thereof.

In addition, the reaction of step 2 may be performed at a temperature of 15 to 30° C., preferably 23 to 28° C.

In the present invention, step 3 may be performed in the presence of a palladium catalyst. The palladium catalyst may be Pd/C, Pd(OH)$_2$, or Pd(OH)$_2$/C.

In step 3, the reaction molar ratio between the compound of formula III, the palladium catalyst and the di-tert-butyl-dicarbonate may be 1:0.03:1 to 1:0.5:5.

Furthermore, a solvent that is used in step 3 is not limited and may be any solvent in which the reaction of step 3 may be performed. For example, the reaction of step 3 may be performed in any one solvent selected from the group consisting of methanol, ethanol, ethyl acetate, tetrahydrofuran, and mixtures thereof.

In addition, the reaction of step 3 may be performed at a temperature of 20 to 35° C., preferably 23 to 28° C.

In the present invention, a base that is used in step 4 above is not limited and may be any base in which the reaction of step 4 may be performed. For example, sodium hydroxide, ammonium hydroxide, potassium hydroxide or lithium hydroxide may be used as the base.

Furthermore, a solvent that is used in step 4 is not limited and may be any solvent in which the reaction of step 4 may be performed. For example, the reaction of step 4 may be performed in purified water, dichloromethane, toluene, ethyl acetate, methyl ethyl ketone, or a mixture solvent thereof.

In addition, the reaction of step 4 may be performed at a temperature of 20 to 40° C., preferably 25 to 35° C.

According to the preparation method of the present invention, optically active tert-butyl 3-methyl-4-oxopiperidine-1-carboxylate (Formula IV) can be prepared, and an optically active drug can be prepared using the prepared compound as an intermediate.

The preparation method of the present invention can prepare highly pure optically active tert-butyl 3-methyl-4-oxopiperidine-1-carboxylate in high yield. In addition, the preparation method of the present invention can industrially produce large amounts of tert-butyl 3-methyl-4-oxopiperidine-1-carboxylate by using commercially available reagents and solvents. Furthermore, since the preparation method of the present invention may comprise racemizing the opposite enantiomer remaining after the preparation of the compound of formula II and using the obtained racemate to prepare the compound of formula I, it can further increase the yield and is economic in that the loss of reagents can be reduced.

The present invention provides a compound of the following formula II and a compound of the following formula III, which are novel intermediates for the preparation of optically active tert-butyl 3-methyl-4-oxopiperidine-1-carboxylate, and methods for preparing the same:

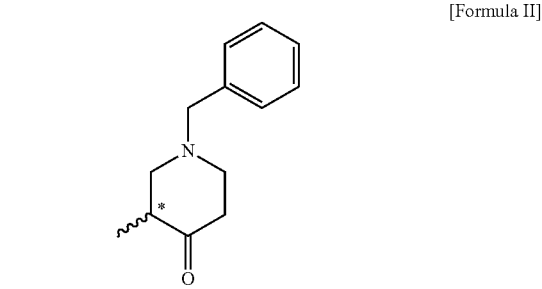

[Formula II]

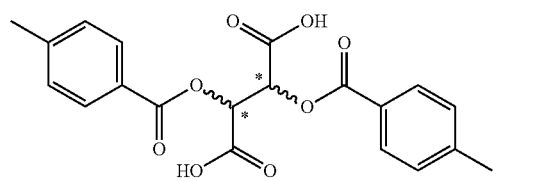

[Formula III]

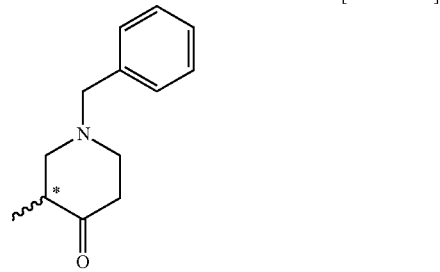

The compound of formula II according to the present invention can be prepared through a step of optically resolving a compound of the following formula I:

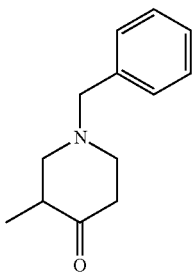

[Formula I]

In the present invention, a method for preparing the compound of formula II may be performed by the same process as the above-described step 1.

In addition, the compound of formula III according to the present invention can be prepared through a step of reacting the compound of formula II with a base. In the present invention, a method for preparing the compound of formula III may be performed by the same process as the above-described step 2.

The compound of formula II and compound of formula III according to the present invention are useful as intermediates for the preparation of optically active tert-butyl 3-methyl-4-oxopiperidine-1-carboxylate.

In the present invention, the compound of formula II is (R)-1-benzyl-3-methylpiperidin-4-one (2S,3S)-2,3-bis((4-methylbenzoyl)oxy)succinate, or (S)-1-benzyl-3-methylpiperidin-4-one (2R,3R)-2,3-bis((4-methylbenzoyl)oxy)succinate. In the present invention, optically active 2,3-bis((4-methylbenzoyl)oxy)succinic acid is used to optically resolve the racemic compound of formula I, and the compound of formula II can be prepared with an optical purity of at least 99% ee and in high yield. In addition, the undesired opposite enantiomer remaining after preparing the compound of formula II can be recycled by simply racemizing it in the presence of a base as mentioned above with respect to step 4 and using the racemate in the preparation of the compound of formula I, thereby increasing the overall process yield and reducing the production cost.

In the present invention, the compound of formula III is (R)-1-benzyl-3-methylpiperidin-4-one, or (S)-1-benzyl-3-methylpiperidin-4-one. In the present invention, the compound of formula III can be prepared with an optical purity of at least 99% ee and in high yield, like the compound of formula II, and thus the desired compound of formula IV can also be prepared with an optical purity of at least 99% ee and in high yield.

Advantageous Effects of Invention

According to the preparation method of the present invention, large amounts of highly pure optically active tert-butyl 3-methyl-4-oxopiperidine-1-carboxylate can be industrially prepared in high yield by use of commercially available reagents and solvents.

In addition, using the novel intermediates of the present invention, highly pure optically active tert-butyl 3-methyl-4-oxopiperidine-1-carboxylate can be prepared in high yield.

BEST MODE FOR CARRYING OUT THE INVENTION

Hereinafter, the present invention will be described in further detail with reference to examples and experimental examples. It is to be understood, however, that these examples and experimental examples are intended to illustrate the present invention and the scope of the present invention is not limited by these examples and experimental examples.

Example 1: Preparation of (R)-1-benzyl-3-methylpiperidin-4-one (2S,3S)-2,3-bis((4-methylbenzoyl)oxy)succinate (Compound of Formula II)

278.0 kg of acetonitrile and 58.9 kg of 1-benzyl-3-methylpiperidin-4-one were introduced into a reactor and warmed to 40±2° C. 129.0 kg of (2S,3S)-2,3-bis((4-methylbenzoyl)oxy)succinic acid hydrate was added thereto. Stirring was performed at 40±2° C. for 12±2 hours. After filtration, the residue was washed with 92.7 kg of acetonitrile. The resulting material was dried under vacuum at 40° C. to afford the title compound (70.7 kg, 83%, 99% ee).

$^1$H-NMR (400 MHz, DMSO-d6): δ=0.84 (d, 3H), 2.16-2.40 (m, 2H), 2.45 (s, 6H), 2.58-2.71 (m, 3H), 3.08-3.11 (m, 2H), 3.74 (s, 2H), 5.79 (s, 2H), 7.27-7.40 (m, 9), 7.89 (d, 4H).

Optical rotation: $[\alpha]_D^{20}$=96.0°

($[\alpha]_D^{20}$: 20° C., D line of sodium spectrum (589 nm), 1% solution)

Example 2: Preparation of (S)-1-benzyl-3-methylpiperidin-4-one (2R,3R)-2,3-bis((4-methylbenzoyl)oxy)succinate (Compound of Formula II)

18.7 kg of acetonitrile and 3.4 kg of 1-benzyl-3-methylpiperidin-4-one were introduced into a reactor and warmed to 40±2° C. 7.4 kg of (2R,3R)-2,3-bis((4-methylbenzoyl)oxy)succinic acid hydrate was added thereto. Stirring was performed at 40±2° C. for 12±2 hours. After filtration, the residue was washed with 5.3 kg of acetonitrile. The resulting material was dried under vacuum at 40° C. to afford the title compound (4.0 kg, 81%, 99% ee).

$^1$H-NMR (400 MHz, DMSO-d6): δ=0.83 (d, 3H), 2.18-2.27 (m, 2H), 2.40 (s, 6H), 2.56-2.72 (m, 3H), 3.09-3.13 (m, 2H), 3.74 (s, 2H), 5.79 (s, 2H), 7.28-7.40 (m, 9), 7.89 (d, 4H).

Example 3: Preparation of (R)-1-benzyl-3-methylpiperidin-4-one (Compound of Formula III)

469.1 kg of dichloromethane and 70.7 kg of the (R)-1-benzyl-3-methylpiperidin-4-one (2S,3S)-2,3-bis((4-methylbenzoyl)oxy)succinate prepared in Example 1 were introduced into a reactor, and 353.5 kg of purified water was added thereto, followed by stirring. The pH was adjusted to 10 by addition of 26.2 L of ammonium oxide. The organic layer was separated and 353.5 kg of purified water was added thereto, followed by stirring. The organic layer was separated, concentrated under vacuum at 40° C., and crystallized from n-heptane to afford the title compound (22.4 kg, 92%, 99.8% ee).

$^1$H-NMR (400 MHz, DMSO-d6): δ=0.85 (d, 3H), 2.03 (t, 1H), 2.16 (d, 1H), 2.33 (t, 1H), 2.53-2.66 (m, 2H), 2.99-3.05 (m, 2H), 3.59 (s, 2H), 7.25-7.35 (m, 5H).

Optical rotation: $[\alpha]_D^{20}$=18.3°

($[\alpha]_D^{20}$: 20° C., D line of sodium spectrum (589 nm), 1% solution).

Example 4: Preparation of (S)-1-benzyl-3-methylpiperidin-4-one (compound of formula III)

26.4 kg of dichloromethane and 4.0 kg of the (S)-1-benzyl-3-methylpiperidin-4-one (2R,3R)-2,3-bis((4-methylbenzoyl)oxy)succinate prepared in Example 2 were introduced into a reactor, and 19.9 kg of purified water was added thereto, followed by stirring. The pH was adjusted to 10 by addition of 1.5 L of ammonium hydroxide. The organic layer was separated and 19.9 kg of purified water was added thereto, followed by stirring. The organic layer was separated and concentrated under vacuum at 40° C. Crystallization from n-heptane was performed to afford the title compound (1.2 kg, 89%, 99.5% ee).

$^1$H-NMR (400 MHz, CDCl$_3$): δ=1.04 (d, 3H), 2.08 (t, 1H), 2.32-2.54 (m, 2H), 2.60-2.78 (m, 2H), 3.03-3.24 (m, 2H), 3.64 (S, 2H), 7.46 (s, 5H).

Example 5: Preparation of tert-butyl (R)-3-methyl-4-oxopiperidine-1-carboxylate (Compound of Formula IV)

141.6 kg of ethyl acetate and 22.4 kg of the (R)-1-benzyl-3-methylpiperidin-4-one prepared in Example 3 were introduced into a hydrogen reactor and completely dissolved by stirring. 28.9 kg of di-tert-butyl dicarbonate and 1.12 kg of 10% palladium/carbon were added thereto, followed by stirring. Stirring was performed for 24 hours under controlled conditions of temperature of 25±2° C. and hydrogen pressure of 50 psi (3.7±0.2 atm). After completion of the reaction, the palladium/carbon was filtered out, and the residue was concentrated under vacuum at 40° C. 15.3 kg of n-heptane was added to the concentrate, followed by cooling to 0±5° C. and crystallization. The resulting material was dried under vacuum at room temperature to afford the title compound (21.4 kg, 91%, 99.5% ee).

$^1$H-NMR (400 MHz, CDCl$_3$): δ=1.02 (d, 3H), 1.47 (s, 9H), 2.36-2.55 (m, 3H), 2.55 (m, 1H), 3.24 (t, 1H), 4.15-4.19 (m, 2H).

Optical rotation: $[α]_D^{20}$=−1.2°

($[α]_D^{20}$: 20° C., D line of sodium spectrum (589 nm), 1% solution).

Example 6: Preparation of tert-butyl (S)-3-methyl-4-oxopiperidine-1-carboxylate (Compound of Formula IV)

7.7 kg of ethyl acetate and 1.2 kg of the (S)-1-benzyl-3-methylpiperidin-4-one prepared in Example 4 were introduced into a hydrogen reactor and completely dissolved by stirring. 1.6 kg of di-tert-butyl dicarbonate and 0.06 kg of 10% palladium/carbon were added thereto, followed by stirring. Stirring was performed for 24 hours under controlled conditions of temperature of 25±2° C. and hydrogen pressure of 50 psi (3.7±0.2 atm). After completion of the reaction, the palladium/carbon was filtered out, and the residue was concentrated under vacuum at 40° C. 1.7 kg of n-heptane was added to the concentrate, followed by cooling to 0±5° C. and crystallization. The resulting material was dried under vacuum at room temperature to afford the title compound (1.0 kg, 78%, 99.2% ee).

$^1$H-NMR (400 MHz, CDCl$_3$): δ=1.02 (d, 3H), 1.47 (s, 9H), 2.34-2.56 (m, 3H), 2.70-2.89 (m, 1H), 3.22 (t, 1H), 4.16-4.19 (m, 2H).

Example 7: Preparation of 1-benzyl-3-methylpiperidin-4-one (Compound of Formula I) by Racemization from Formula ent-II and Formula II (Recycle)

The filtrate remaining after preparing the compound of formula II (Example 1) was introduced into a reactor and concentrated under vacuum at 45° C. The concentrate was cooled to 0 to 5° C., and 83 L of 10% NaOH aqueous solution was added slowly thereto. The reaction solution was warmed to 35 to 40° C. and stirred for 6 hours. 221.9 kg of dichloromethane was added thereto, followed by stirring for 30 minutes, after which the organic layer was separated. 133.4 kg of dichloromethane was added to the aqueous layer, followed by stirring for 30 minutes, after which the organic layer was separated. 59 kg of anhydrous magnesium sulfate was added to the organic layer and stirred for 30 minutes, followed by filtration. The residue was concentrated under vacuum at 40° C. to afford the title compound (23.6 kg, 80%).

$^1$H-NMR (400 MHz, CDCl$_3$): δ=0.85 (d, 3H), 2.02 (t, 1H), 2.16 (d, 1H), 2.32 (t, 1H), 2.50-2.67 (m, 2H), 2.98-3.23 (m, 2H), 3.58 (s, 2H), 7.23-7.36 (m, 5H).

Example 8: Preparation of 1-benzyl-3-methylpiperidin-4-one (Compound of Formula I) by Racemization from Formula Ent-II and Formula II (Recycle)

The filtrate remaining after preparing the compound of formula II (Example 2) was introduced into a reactor and concentrated under vacuum at 45° C. The concentrate was cooled to 0 to 5° C., and 4.8 L of 10% NaOH aqueous solution was added slowly thereto. The reaction solution was warmed to 35 to 40° C. and stirred for 6 hours. 12.8 kg of dichloromethane was added thereto, followed by stirring for 30 minutes, after which the organic layer was separated. 12.8 kg of dichloromethane was added to the aqueous layer, followed by stirring for 30 minutes, after which the organic layer was separated. 7.7 kg of dichloromethane was added to the aqueous layer, followed by stirring for 30 minutes, after which the organic layer was separated. 3.4 kg of anhydrous magnesium sulfate was added to the organic layer and stirred for 30 minutes, followed by filtration. The residue was concentrated under vacuum at 40° C. to afford the title compound (1.3 kg, 75%).

$^1$H-NMR (400 MHz, CDCl$_3$): δ=0.85 (d, 3H), 2.02 (t, 1H), 2.16 (d, 1H), 2.32 (t, 1H), 2.50-2.67 (m, 2H), 2.98-3.23 (m, 2H), 3.58 (s, 2H), 7.23-7.36 (m, 5H).

The invention claimed is:
1. A compound of the following formula II:

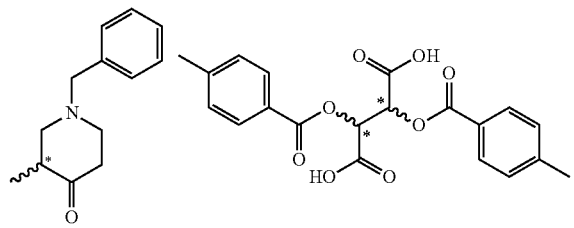

[Formula II]

2. The compound of claim 1, wherein the compound of formula II is
- (R)-1-benzyl-3-methylpiperidin-4-one (2S,3S)-2,3-bis((4-methylbenzoyl)oxy)succinate; or
- (S)-1-benzyl-3-methylpiperidin-4-one (2R,3R)-2,3-bis((4-methylbenzoyl)oxy)succinate.
3. A method for preparing a compound of the following formula II, comprising a step of optically resolving a compound of the following formula I:
[Formula I]
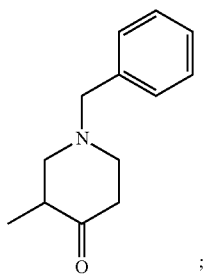
[Formula II]
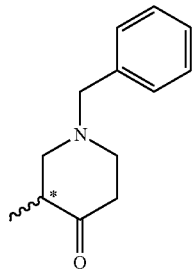
* * * * *